United States Patent [19]

Malka

[11] Patent Number: 5,196,012
[45] Date of Patent: Mar. 23, 1993

[54] EXTERNAL COMPRESSION FRAME RAPIDLY STABILIZING UNSTABLE PELVIC FRACTURES

[76] Inventor: Jeffrey S. Malka, 6845 Elm St., McLean, Va. 22101-3889

[21] Appl. No.: 728,576

[22] Filed: Jul. 11, 1991

[51] Int. Cl.⁵ .............................................. A61F 5/04
[52] U.S. Cl. ........................................ 606/54; 606/57
[58] Field of Search ................................ 606/54–59, 606/105

[56] References Cited

U.S. PATENT DOCUMENTS

| | | |
|---|---|---|
| 4,157,715 | 6/1979 | Westerhoff ................ 606/58 X |
| 4,361,144 | 11/1982 | Slatis et al. . |
| 4,615,338 | 10/1986 | Ilizarov et al. ................ 606/58 |
| 4,815,455 | 3/1989 | Kim . |

FOREIGN PATENT DOCUMENTS 888979 12/1981 U.S.S.R. .
1050694 10/1983 U.S.S.R. .
1149960 4/1985 U.S.S.R. .

OTHER PUBLICATIONS

Ganz et al., "The Antishock Pelvic Clamp", Clinical Orthopaedics and Related Research, 267 (U.S.A. Jun. 1991).
Osteotaxis Brochure, Jun. 1977.

*Primary Examiner*—Robert A. Hafer
*Assistant Examiner*—Sam Rimell

[57] ABSTRACT

An external fixator frame for reducing pelvic fractures consisting of a rectangular horizontal frame connecting to the pelvis through removable pins (FIG. 2). A ratchet or compressive horizontal arm of the frame is used to rapidly insert the pins into the pelvis and simultaneously reduce the pelvic fracture by applying compression across it. The rapidity and simplicity of application permits early use in an emergency setting prior to other studies and treament modalities.

16 Claims, 1 Drawing Sheet

EXTERNAL COMPRESSION FRAME RAPIDLY STABILIZING UNSTABLE PELVIC FRACTURES

FIELD OF INVENTION

This invention relates to external fixators for pelvic fractures.

BACKGROUND

Trauma Centers and Emergency Rooms dealing with Multiple Trauma Patients are often faced with a patient with an unstable Pelvic fracture and associated injuries. These pelvic fractures are a cause of severe life threatening bleeding especially in a multi-trauma situation. Trauma surgeons know that it is essential to stabilize these pelvic fractures rapidly to decrease intra-pelvic bleeding and reduce mortality. This early stabilization is usually done using an external fixator. The need for early use of an external fixator as a life saving measure by reducing intra-pelvic bleeding is widely accepted by trauma surgeons. The problem is that applying the presently available external fixators is not a simple or rapid procedure, even to experienced trauma orthopedic surgeons. Available fixators were designed to attempt to stabilize both anterior and posterior components of the pelvic fracture. Clinical studies have repeatedly shown however that they are incapable of stabilizing the posterior pelvis which usually requires late open surgery. All they can hope to achieve is to close the anterior gaping (open book deformity) and for this purpose a simpler device such as mine that can be rapidly applied is all that is necessary. Presently available fixators often require an incision over the iliac crest to identify the plane of the iliac wing since this plane varies from patient to patient. This is followed by the drilling of multiple fixator pins (30) parallel to the narrow plane of the iliac wings (FIG. 4). Said drilling is difficult to achieve, often requiring repeated efforts and frequently risks either missing the narrow iliac wing bone and, or, injuring intra pelvic organs (34). Further, the said insertion procedure is risky in the unsterile surroundings of an emergency room, especially if the incision accidentally communicates with the frequently present intra-pelvic hematoma—thereby dangerously rendering a treatable closed pelvic fracture into a lethal contaminated "open" pelvic fracture. It is for this reason that these patients are often taken to the operating room for application of external fixators, with subsequent delay of application of this frequently life-saving measure. Even in the operating room it is hard to apply an external fixator in less than 30–60 minutes under the most favorable circumstances and often much longer, further delaying all subsequent measures and costing lives. There therefore is a great need for a simple external fixator that can be safely applied in a unsterile Emergency Room, and applied rapidly without delaying or compromising subsequent steps in the evaluation and treatment of these multiply injured patients.

OBJECTS AND ADVANTAGES

My invention is such a simple and rapidly appliable external fixator which I am naming a "Pelvic Rapid Fixator". It combines the principles of skull traction pins (which are routinely applied without skin incisions in Emergency Rooms) and a ratchet or compression means. It could be applied in less than 5 minutes in an emergency room, be manufactured of cat scan and magnetic resonance imaging compatible materials, be partially disposable (the pins) and rapidly become an essential and inexpensive routine tool in all ER and Trauma Centers dealing with severe trauma. My pins (32) attach lateral to the pelvic iliac wings (FIGS. 3 and 4), instead of parallel to the said narrow bone, (FIG. 4) as is the case in prior art, thus eliminating the risk of missing the bone partially or totally. My pins are not drilled or hammered in, as in prior art (U.S. Pat. Nos. 4,361,144, 4,815,455, and Foreign Pats SU-888-979, SU 1050-694-A, HJ 1012 D) and thus can be applied more rapidly and with no risk of intra-pelvic organ injury. My pins require either no incision or at most a 1 centimeter incision, thus permitting their safe application in an unsterile surrounding such as an emergency room. The compressive horizontal arm permits very rapid and effective compression reducing the fracture and maintaining the pins well attached to bone. The hinges on the frame permit swinging the horizontal compression arm of the frame as needed, either downwards towards the feet to provide surgical clearance to the abdominal wall, or towards the head to provide clearance to the lower pelvis. The ease and rapidity of application will cause the device to be used early when it is most needed resulting in the saving of many lives.

The Antishock Pelvic Clamp described by Reinhold Ganz, et al in Clinical Orthopaedics and Applied Research, 267:71, June 1991 requires the drilling or hammering in of Steinmann pins, which may perforate organs either during the drilling or subsequently as the pins migrate with time and motion which such pins are well known to do. Said device also has a complicated means of applying compression using threaded bolts and wrenches. Further the said Ganz device is designed to be applied over the posterior pelvis. This location has several severe disadvantages namely: there is about 3–4 inches of muscle between skin and bone at that location, thus necessitating a considerable incision. Pins placed at this posterior location contaminate the area of the pelvis where a surgical incision for subsequent definitive surgery is usually needed thus making such future surgery at great risk of becoming infected. My frame avoids these problems by being designed for anterior application where there is very little tissue between the bone and the skin and where contamination will not disrupt future surgical incisions. Further no drilling or hammering is needed and thus no excessive penetration is possible due to the design of the pins.

DRAWING FIGURES

REFERENCE NUMERALS IN DRAWINGS

Figure 1:
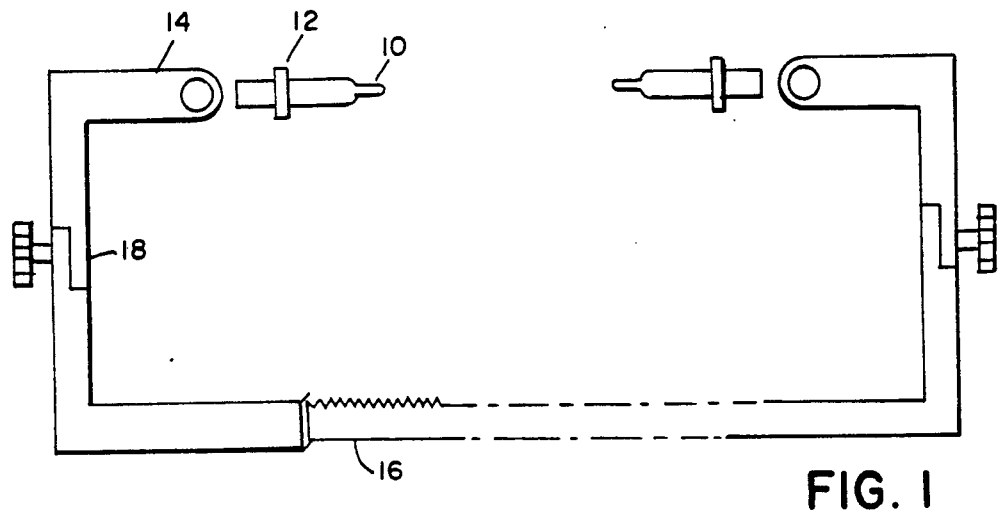
FIG. 1 illustrates a horizontal view of the frame and pins
Figure 2:
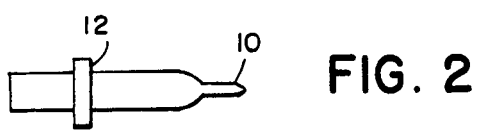
FIG. 2 illustrates detail of the pins
Figure 3:
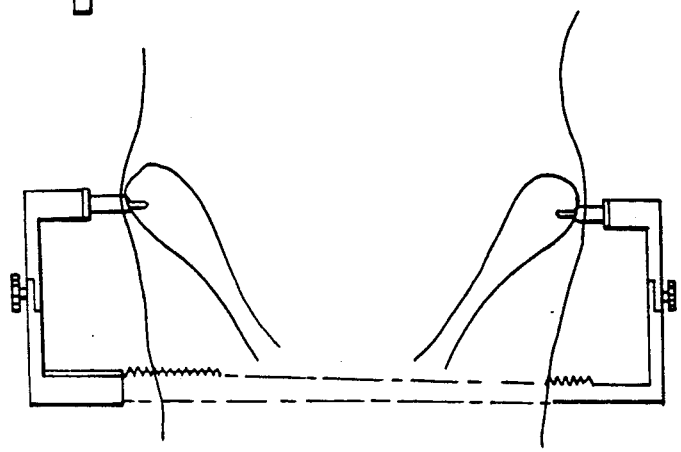
FIG. 3 illustrates the frame as applied to the pelvis
Figure 4:
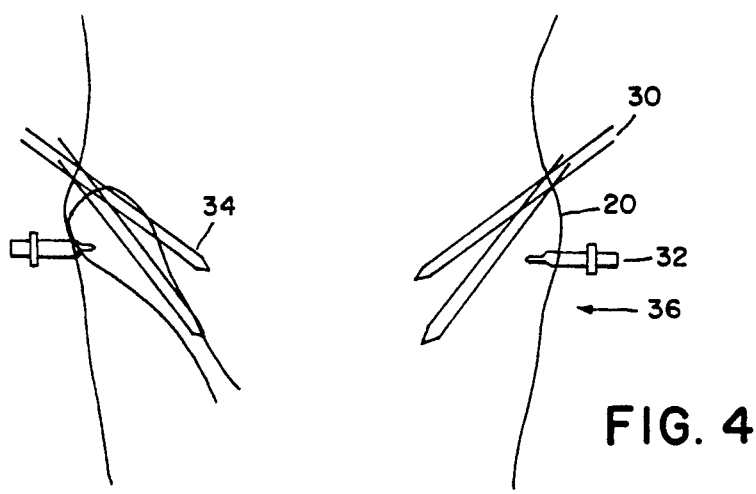
FIG. 4 illustrates placement of pins in most presently available external fixators compared with my pins

10 Steinmann type tip
12 Buttress
14 Female end of frame designed to accept insertion of pin cylinder
16 Compressive or ratcheted horizontal arm of frame
18 Hinge
20 Anterior superior iliac spine of pelvis
30 other pins from prior art
32 my pins
34 protrusion of other pins to injure pelvic organs 36 direction of compressive force in my device

DESCRIPTION OF THE "PELVIC RAPID FIXATOR"

The pins consist of a cylinder ending in a Steinmann type tip (10) and a buttress (12). The end opposite the Steinmann tip is designed to enter the receiving socket of the main frame (14). The buttress (12) can be eliminated if the pin receiving socket (14) of the main frame is a closed ended hollow cylinder permitting only a predetermined amount of penetration of the pin cylinder.

The main frame consists of 2 halves of a rectangle attached together by a ratchet or other compressive means (16). On each of the short arms of the main frame an optional hinge (18) is present to permit angling the compressive horizontal arm of the frame (18) towards the head or feet as needed.

OPERATION

The entire system is very intuitive and simple to use with almost no learning curve and should be able to be applied in less than 5 minutes even by a novice. The pins would grip the anterior iliac crest (20) where it is easily palpable. The only preparation necessary would be a skin disinfectant and possibly some local anaesthetic injection. Then the sterile pins would be inserted into their receiving ends in the main frame (14). One pin would be pressed against the easily palpable anterior superior iliac spine of the pelvis (20) either directly through the skin or after a 1 centimeter incision. The ratchet or compressive device (16) would then be tightened thereby bringing the other opposite pin in contact with the opposite anterior superior iliac spine. Further rapid compression would cause simultaneous penetration of the pins into the bone and reduction of the deformity commonly associated with pelvic fractures. The device's application should not compromise any subsequent planned cat scan, magnetic resonance, x-ray studies or surgery.

CONCLUSION, RAMIFICATIONS, AND SCOPE OF INVENTION

Thus the reader will see that the "Pelvic Rapid Fixator" here described provides the ability to very rapidly, simply, and inexpensively stabilize a fractured pelvis in an unsterile emergency room, without the need of an operating room and with minimal training. The rapidity and simplicity of application would permit the said device to be applied very early in the treatment of such patients, reducing shock and saving lives.

While my above description contains many specificities, these should not be construed as limitations on the scope of the invention, but rather as an exemplification of one preferred embodiment thereof. Many other variations are possible. For example, the main frame could have more than one pin receiving socket (14) on each side, with a total of 4 or more pins per pelvis. The material the frame and pins are manufactured of could be metal, or magnetic resonance imaging compatible, or x-ray compatible, or carbon fiber, or plastic, or any combination thereof. The frame could have a hinge or not. The pins could have a buttress or not and could be cylindrical or not. The compressive means could be any type of ratchet or other compressive means. An additional clamp or screw could be added to the compressive horizontal arm to prevent inadvertent loss of compression by slippage after it is applied.

I claim:
1. A device to stabilize a fractured pelvis using
   a) at least two substantially oppositely axially aligned pins that attach to the lateral wall of the bony pelvis;
   b) an external frame with first and second arms having receiving sockets for said pins and having a compressive means comprising a ratchet means for simultaneously compressing the said pins and said attached pelvis;
   said device for rapidly applying without need for sterile surroundings or operating room and with minimal training,
   and for rapidly stabilizing said pelvis in an emergency setting for reducing intrapelvic bleeding and pain and permitting further diagnostic studies, xrays, and surgery to be undertaken safely.

2. A device as in claim 1, in which each of the the arms of the said frame include hinges to permit angling the arm, of the said main frame.

3. A device to stabilize pelvic fractures by applying a lateral compressive force to the anterior pelvis comprising substantially oppositely axially aligned pins for applying compressive pressure through lateral walls of the pelvis, a main frame having arms connected to the pins and having a ratchet for rapidly applying said device without the need for sterile surroundings or operating room and with minimal training,
   and rapidly stabilizing said pelvis in an emergency setting for reducing intrapelvic bleeding and pain and permitting further diagnostic studies, xrays, and surgery to be undertaken safely.

4. A device as in claim 3, in which the arms of the main frame include hinges to permit angling a horizontal arm of the said main frame.

5. Apparatus for stabilizing pelvic fractures, comprising a frame having first and second opposed spaced socket members having first and second substantially oppositely axially aligned sockets receiving first and second substantially axially aligned opposed spaced pins for exterior attachment to opposite anterior iliac crests of a fractured pelvis, first and second arms connected to the first and second socket members, and a ratchet compressive means attached to the first and second arms remote from the socket members for holding the socket members inwardly for applying compressive pressure from the ratchet compressive means through the arms, socket members and pins for applying compressive pressure to opposite iliac crests.

6. The apparatus of claim 5, wherein each of the arms has a first socket-connecting section and a second ratchet connecting section, and a hinge interconnecting the sections for fixedly interconnecting the sections in angular relationships.

7. The apparatus of claim 5, wherein the ratchet means comprises a telescoping connector.

8. The apparatus of claim 5, wherein the socket members, the arms and the ratchet compressive means form a rectangular frame.

9. The apparatus of claim 8, wherein the ratchet compressive means comprises a telescoping tubular arm.

10. The apparatus of claim 5, wherein the socket members comprise tubular members having circular end openings, and wherein the pins comprise cylindrical bodies having first pelvic attachment ends and second mounting ends for mounting in the circular openings, and wherein the pins comprise intermediate radially extending buttresses for engaging ends of the socket members outside of the pin-receiving openings.

11. Apparatus for stabilizing pelvic fractures, comprising a frame having first and second opposed spaced socket members having first and second substantially oppositely axially aligned sockets receiving first and second substantially axially aligned opposed spaced pins for exterior attachment to opposite anterior iliac crests of a fractured pelvis, first and second lateral arms having first and second hingedly connected sections, said first sections connected to the first and second socket members, and a compressive means attached to the second sections of the first and second lateral arms remote from the socket members for holding the socket members inwardly for applying compressive pressure from the compressive means through the arms, socket members and pins for applying compressive pressure to opposite iliac crests, wherein the second sections of the lateral arms are angularly movable with respect to the first sections.

12. The apparatus of claim 11, wherein hinges interconnecting the first and second sections of the lateral arms interconnects the sections for fixedly positioning the sections and the compressive means in angular relationships.

13. The apparatus of claim 11, wherein the compressive means comprises a telescoping connector.

14. The apparatus of claim 11, wherein the socket members, the lateral arms and the compressive means form a rectangular frame.

15. The apparatus of claim 8, wherein the compressive means comprises a telescoping tubular arm.

16. The apparatus of claim 11, wherein the socket members comprise tubular members having circular end openings, and wherein the pins comprise cylindrical bodies having first pelvic attachment ends and second mounting ends for mounting in the circular openings, and wherein the pins comprise intermediate radially extending buttresses for engaging ends of the socket members outside of the pin-receiving openings.

* * * * *